(12) United States Patent
Kratzer et al.

(10) Patent No.: US 10,433,724 B2
(45) Date of Patent: Oct. 8, 2019

(54) METHOD AND APPARATUS FOR DETERMINING THE LOCATION OF THE OCULAR PIVOT POINT

(71) Applicant: Carl Zeiss Vision GmbH, Aalen (DE)

(72) Inventors: Timo Kratzer, Aalen (DE); Jesus-Miguel Cabeza-Guillen, Aalen (DE); Gerhard Kelch, Aalen (DE)

(73) Assignee: Carl Zeiss Vision GmbH, Aalen (DE)

( * ) Notice: Subject to any disclaimer, the term of this patent is extended or adjusted under 35 U.S.C. 154(b) by 0 days.

(21) Appl. No.: 14/459,154

(22) Filed: Aug. 13, 2014

(65) Prior Publication Data
US 2014/0354948 A1    Dec. 4, 2014

Related U.S. Application Data

(63) Continuation of application No. 13/219,447, filed on Aug. 26, 2011, now Pat. No. 8,840,247, which is a continuation of application No. PCT/EP2010/000698, filed on Feb. 4, 2010.

(30) Foreign Application Priority Data

Feb. 26, 2009    (DE) .......................... 10 2009 010 467

(51) Int. Cl.
*A61B 3/11*    (2006.01)
*A61B 3/113*   (2006.01)
*A61B 3/10*    (2006.01)

(52) U.S. Cl.
CPC ............... *A61B 3/111* (2013.01); *A61B 3/113* (2013.01); *A61B 3/1005* (2013.01)

(58) Field of Classification Search
CPC . A61B 3/11; A61B 3/111; A61B 3/112; A61B 3/113; A61B 3/14; A61B 3/145; A61B 3/1005; G02C 7/027; G02C 7/028

USPC ........... 359/159.42, 159.73, 159.74, 159.75, 359/159.76, 159.77, 204–210, 212, 246, 359/247; 396/18

See application file for complete search history.

(56) References Cited

U.S. PATENT DOCUMENTS

| 4,105,302 A * | 8/1978 | Tate, Jr. ................ A61B 3/028 351/210 |
| 4,613,217 A | 9/1986 | Fuerter et al. |

(Continued)

FOREIGN PATENT DOCUMENTS

| CN | 101219077 A | 7/2008 |
| DE | 10 2005 041 710 A1 | 3/2007 |

(Continued)

OTHER PUBLICATIONS

Thibos, L. et al, "Clinical Applications of the Shack-Hartmann Aberrometer", Optometry and Vision Science, vol. 76, No. 12, Dec. 1999, pp. 817 to 825, American Academy of Optometry.

(Continued)

*Primary Examiner* — William R Alexander
*Assistant Examiner* — Gary W O'Neill
(74) *Attorney, Agent, or Firm* — Walter Ottesen, P.A.

(57) ABSTRACT

The invention relates to a method and an apparatus for determining the location of at least two optical parameters of an eye of a test person. In the method, at least two optical parameters of an eye having a reference structure are photographically recorded to determine in each case one of the optical parameters of the eye. The apparatus for determining at least two optical parameters of an eye having a reference structure is provided with separate recording units for photographically recording the eye for the determination of in each case one of the optical parameters of the eye.

11 Claims, 8 Drawing Sheets

(56) References Cited

U.S. PATENT DOCUMENTS

| | | | |
|---|---|---|---|
| 5,016,282 A | 5/1991 | Tomono et al. | |
| 5,444,503 A | 8/1995 | Kelch et al. | |
| 5,818,954 A | 10/1998 | Tomono et al. | |
| 5,963,300 A | 10/1999 | Horwitz | |
| 6,089,713 A | 7/2000 | Hof et al. | |
| 6,193,371 B1 | 2/2001 | Snook | |
| 6,234,631 B1 | 5/2001 | Sarver et al. | |
| 6,241,355 B1 | 6/2001 | Barsky | |
| 6,276,798 B1* | 8/2001 | Gil | A61B 5/0059 351/206 |
| 6,580,448 B1 | 6/2003 | Stuttler | |
| 6,637,880 B1 | 10/2003 | Yamakaji et al. | |
| 6,871,955 B2 | 3/2005 | Yamakaji et al. | |
| 7,043,056 B2 | 5/2006 | Edwards et al. | |
| 7,216,980 B2 | 5/2007 | Mihashi et al. | |
| 7,472,992 B2 | 1/2009 | Altheimer et al. | |
| 7,637,614 B2 | 12/2009 | Berthezene et al. | |
| 7,740,355 B2 | 6/2010 | Sessner et al. | |
| 7,794,085 B2 | 9/2010 | Bonnin et al. | |
| 8,048,065 B2 | 11/2011 | Grecu et al. | |
| 8,182,087 B2 | 5/2012 | Esser et al. | |
| 9,994,228 B2* | 6/2018 | Krueger | A61M 21/00 |
| 2003/0123026 A1* | 7/2003 | Abitbol | G02C 13/003 351/204 |
| 2003/0223037 A1 | 12/2003 | Chernyak | |
| 2004/0189935 A1* | 9/2004 | Warden | G02C 7/027 351/204 |
| 2005/0134799 A1 | 6/2005 | Thompson et al. | |
| 2006/0189966 A1 | 8/2006 | Lieberman et al. | |
| 2007/0025642 A1 | 2/2007 | Buckland et al. | |
| 2007/0242218 A1 | 10/2007 | Berthezene et al. | |
| 2010/0128220 A1 | 5/2010 | Chauveau | |
| 2010/0145489 A1 | 6/2010 | Esser et al. | |
| 2010/0149484 A1 | 6/2010 | Berthezene et al. | |
| 2010/0172567 A1* | 7/2010 | Prokoski | A61B 5/0064 382/132 |
| 2011/0149239 A1* | 6/2011 | Neal | A61B 3/0025 351/205 |
| 2012/0127429 A1 | 5/2012 | Grecu et al. | |
| 2014/0009737 A1* | 1/2014 | Kweon | A61B 3/111 351/204 |
| 2019/0053701 A1* | 2/2019 | Neal | A61B 3/0025 |

FOREIGN PATENT DOCUMENTS

| | | |
|---|---|---|
| EP | 1 767 174 A2 | 3/2007 |
| EP | 2 020 205 A1 | 2/2009 |
| JP | 02-121620 | 5/1990 |
| JP | 02-134130 A | 5/1990 |
| JP | 11-137524 A | 5/1999 |
| JP | 2000-300520 A | 10/2000 |
| JP | 2004-8768 A | 1/2004 |
| JP | 2008-70894 A | 3/2008 |
| JP | 2008070894 A | 3/2008 |
| JP | 2008246004 A | 10/2008 |
| WO | 03/101341 A2 | 12/2003 |

OTHER PUBLICATIONS

Grimm W. et al, "Gradal^R Individual: Design, Production and Fitting", reprint of article in Deutsche Optikerzeitung, issues 4 and May 2000.

English translation of the Office action of the German Patent Office dated Jan. 15, 2010 in German patent application 10 2009 010 467.4 on which the claim of priority is based.

International Search Report dated Jun. 1, 2010 of international application PCT/EP 2010/000698 on which this application is based.

International Search Report of the European Patent Office dated Jun. 10, 2010 of international application PCT/EP 2010/000698 on which this application is based.

English translation of International Preliminary Report on Patentability and Written Opinion of the international searching authority dated Aug. 30, 2011 in international patent application PCT/EP2010/000698 on which the claim of priority is based.

European Search Report dated May 14, 2012 of parallel European application 12 00 2380.

English translation and European Office action dated Sep. 12, 2013 of parallel European application 12 002 380.9.

English translation and Chinese Office action dated Sep. 13, 2013 of parallel Chinese application 201080009457.9.

Partial English translation and Japanese Office action dated Oct. 22, 2013 of parallel Japanese application 2011-551429.

English translation of Chinese Office action dated May 30, 2014 of parallel Chinese application 201080009457.9.

English translation and German Office action dated Nov. 3, 2014 of a parallel German application.

English translation of Chinese Office Action dated Aug. 5, 2015 of corresponding Chinese application 201410399688.5.

English translation and Chinese Office action dated Jun. 24, 2015 of corresponding Chinese application 201410399687.0.

English translation of Japanese Office action dated Mar. 23, 2015 of corresponding Japanese application 2014-088827.

English translation of Chinese Office action dated Jul. 27, 2015 of corresponding Chinese application 201410399662.0.

English translation and Second Chinese Office action dated Feb. 5, 2016 of corresponding Chinese application 201410399662.0.

English translation and Second Chinese Office action dated Jun. 20, 2016 of corresponding Chinese application 201410399688.5.

English translation and Japanese Office action dated Jul. 5, 2016 of corresponding Japanese application 2015-176333.

English translation of Chinese Office action dated Feb. 22, 2017 of corresponding Chinese application 201410399688.5.

Imai et al: Rotation Vector Analysis of Eye Movement in Three Dimensions with an Infrared CCD Camera, Acta Otolaryngol, Stockholm, 1999, 119, p. 24 to 28.

English translation and Extended Search Report of the European Patent Office dated Sep. 18, 2017 in corresponding European patent application 17175172.0-1657.

English translation and Chinese Office action dated Aug. 31, 2017 of parallel Chinese application 201410399688.5.

English translation and Extended Search Report of the European Patent Office dated Oct. 16, 2017 in corresponding European patent application 17178300.4-1657.

English translation and European Office action dated Sep. 5, 2018 of corresponding European application 17175172.0-1115.

English translation of extended European Office action dated Oct. 16, 2017 of corresponding European application 17178300.4-1657.

English translation and German Office action dated Feb. 8, 2019 of corresponding German application 10 2009 010 467.4.

English translation of DIN 5340, German standard, Terms of physiological optics, Normenausschuss Feinmechanik und Optik (NAFuO) im DIN Deutsches Institut fuer Normung e.V., Apr. 1998, pp. 1 to 51.

* cited by examiner

Compute ADL

METHOD AND APPARATUS FOR DETERMINING THE LOCATION OF THE OCULAR PIVOT POINT

CROSS REFERENCE TO RELATED APPLICATIONS

This application is a continuation application of patent application Ser. No. 13/219,447, filed Aug. 26, 2011, which is, in turn, a continuation application of international patent application PCT/EP 2010/000698, filed Feb. 4, 2010, designating the United States and claiming priority from German application 10 2009 010 467.4, filed Feb. 26, 2009, and the entire content of the above applications is incorporated herein by reference.

FIELD OF THE INVENTION

The invention relates to methods for determining the location of the ocular pivot point in an eye of a test person.

The invention further relates to methods for optimizing a spectacle lens customized for an eye in which the location of the ocular pivot point is determined and used as input parameter.

Finally, the invention relates to a method for determining at least two optical parameters of an eye having a reference structure wherein the eye is recorded photographically by separate recording units to determine corresponding ones of the parameters.

The invention further relates to apparatus for carrying out the above-named methods.

BACKGROUND OF THE INVENTION

In order to optimize spectacle lenses, in particular customized progressive lenses, it is known to take account of various parameters of the eye/spectacles system. These parameters are, for example, the pupil distance PD, the corneal vertex distance HSA, the forward inclination angle $\alpha$ of the spectacle lens, the frame disk angle ($\alpha_R$, $\alpha_L$) for the right-hand and left-hand spectacle lens, as well as the location of the optical or mechanical ocular pivot point (Z', M). Customized progressive lenses are understood to be progressive lenses in the case of which at least one individual use parameter is taken into account when calculating the spectacle lens, and which are fabricated by means of free-form technology, as this is described, for example, in the Deutsche Optikerzeitung DOZ 4+5/2000 by W. Grimm and G. Kelch in the article "Gradal® Individual: Konzeption, Fertigung and Anpassung", [Gradal® Customized: design, fabrication and adjustment"], in U.S. Pat. 6,089,713 and/or in U.S. Pat. No. 5,444,503.

In the case of non-customized spectacle lenses, these parameters are determined from statistical mean values of a representative cross section of the population. By contrast, in the case of customized spectacle lenses the parameters are measured individually on the respective spectacle wearer, for example, with the aid of so-called video centering systems such as are produced and marketed by Carl Zeiss Vision GmbH of Aalen, Germany, under the product designations of "i.Terminal" and "Relaxed Vision Terminal". However, these video centering systems are so far not in a position to be able to optimize the spectacle lens with the aid of the location of the ocular pivot point in a sufficiently exact way.

If it is desired to take account of the location of the ocular pivot point, the location can be derived in a known way from the eye length via the mean sphere of the prescribed spectacle lens. However, in this case many assumptions are made that do not sufficiently correspond to the actual circumstances.

The relationship between eye length and the sphere of the prescribed spectacle lens is frequently assumed for simplicity as being linear. However, this is not the case in reality, because both the curvature of the cornea and the eye lens as well as the eye length increase very independently of one another and/or develop differently.

It is sufficient in general to regard the ocular pivot point as a point pivot center inside the eye. However, the invention also comprises in very general terms an extended, generally approximately spherical, ocular pivot point zone. For the sake of simplicity, unless otherwise mentioned, a point ocular pivot point is the starting point below for describing the invention and the prior art.

The usual procedure for prescribing spectacles is for the spectacle lenses to be prescribed and centered on the basis of a subjective refraction and a video centering measurement.

It is disadvantageous in this that there is no referencing between the determination of refraction and the centering, because the two operations are carried out by different apparatus. For example, when the refraction is determined with the aid of a phoropter, it can happen that the phoropter is tilted by a first angle relative to the line that connects the two pupil centers of the eye. Furthermore, it can happen that the selected spectacle frame is rotated relative to this line by a second angle. In the most unfavorable case, the two angles can add up, and this can lead to a discrepancy of a plurality of angular degrees in the axes of the cylinders between the prescription and the correction done on the finished spectacles.

U.S. Pat. No. 7,794,085 discloses a method and an apparatus for determining the location of the ocular pivot point. In the case of this known method, a test person looks into a unit resembling a telescope. The alignment of the unit in space is determined by a three-dimensionally active sensor located on the unit. The test person wears on his head a further such sensor, which determines the position and alignment of his head. Located in the unit on the side averted from the test person is a light source that emits a light ray along an optical axis. Located between the light source and the eye of the test person are two gratings with central marks. The test person now moves the unit until the light ray and the two marks coincide. The position of the viewing axis in space is calculated from the position data found in this case for the unit and the head. The operation is then repeated several times from different viewing directions so that a plurality of viewing axes are determined. The pivot point is then calculated as the location of the ocular pivot point.

This known procedure has the disadvantages that there is a need for a substantial outlay on separate units. Furthermore, the measuring accuracy depends on the subjective behavior of the test person.

U.S. Pat. No. 6,580,448 discloses a method and an apparatus for acquiring visual information in parallel. In a fixed alignment and position of the head of the test person, in order to determine the location of the ocular pivot point in the case of this known procedure the fixation line is determined for at least two known fixation points fixated successively by the eyes. The fixation points are two marking points that can be permanently connected to the holder of cameras and sensors in order to determine the pupil position. The ocular pivot point then lies at the intersection of the fixation lines defined by the fixation points.

SUMMARY OF THE INVENTION

It is the object of the invention to provide other methods for determining the location of the ocular pivot point. Furthermore, an object is to provide a method enabling a common spatial reference to be found for the measured values during the detection of parameters of the eye/spectacles system with the aid of a plurality of different measurements, in particular by using different units.

In the case of a first one of the methods mentioned at the beginning, this object is achieved according to the invention by the steps of:
- a) determining the mean curvature of the cornea of the eye;
- b) determining the mean phase error of the eye;
- c) determining the eye length from the mean curvature and the mean phase error; and,
- d) determining the location of the ocular pivot point from the eye length.

The mean curvature of the cornea designates the mean value of the curvature of the cornea in the region of the corneal vertex, generally in a circular region of the radius 4 mm about the corneal vertex. The phase error of the eye is the deviation of the phase of a wavefront emerging from the eye from a reference wave, here, in general, from a plane wavefront. The mean phase error designates the mean curvature of the wavefront. The eye length is the geometric length of the eye between the corneal vertex and the fovea. The location of the ocular pivot point is understood very generally as the site of the optical ocular pivot point. According to DIN 5340-43, for example, the foot of the perpendicular from the mechanical ocular pivot point to the fixation line extended into the interior of the eye in the case of viewing directly onto an infinitely remote point when head and body are held relaxed is taken as the optical ocular pivot point (symbol Z'). According to DIN 5340-42, for example, the mechanical ocular pivot point (symbol M) is that point in the eye that is displaced the least during viewing movements.

In the case of another, second one of the methods mentioned at the beginning, this object is achieved according to the invention by the steps of:
- a) determining the position and/or the shape of a characteristic part of the eye for at least two viewing directions, that is to say, by contrast with the disclosure of U.S. Pat. No. 6,580,448, not permanently prescribed markings and/or not a fixed position of the head;
- b) detecting the position of at least one characteristic axis of the eye for the two viewing directions from the respective position and/or the respective shape of the characteristic part of the eye, for the two viewing directions; and,
- c) determining the location of the ocular pivot point from the position of the at least one characteristic axis of the eye for the two viewing directions.

In the case of a further, third one of the methods mentioned at the beginning, this object is achieved according to the invention by the steps of:
- a) measuring in three dimensions at least a portion of the surface of the cornea of the eye for a first viewing direction of the test person;
- b) describing the surface of the cornea determined in step a) by a three-dimensional mathematical formula;
- c) measuring in three dimensions at least a portion of the surface of the cornea for a viewing direction of the test person altered by comparison with the viewing direction in step a), doing so at the same measurement position as for step a), for a head position of the test person unchanged by comparison with step a); and,
- d) determining the viewing direction in step c) and/or the location of the ocular pivot point by fitting the three-dimensional data measured in step c) to the formula determined in step b), use being made of a mathematical transformation, in particular rotation about a point in space.

In the case of a fourth one of the methods mentioned initially herein, this object is achieved according to the invention by virtue of the fact that the reference structure of the eye is recorded in each case at the same time during the photographic recordings, and that the values of the parameters are referred to the reference structure.

The object on which the invention is based is, furthermore, achieved by apparatus for carrying out the above-named methods.

In particular, a first one of the apparatus mentioned initially herein for determining the location of the ocular pivot point in an eye of a test person is characterized by:
- a) a curvature determination device for determining the mean curvature of the cornea of the eye;
- b) a phase error measurement device for determining the mean phase error of the eye;
- c) an eye length calculation device for determining the eye length from the mean curvature and the mean phase error; and,
- d) an ocular pivot point determination device for determining the location of the ocular pivot point from the eye length.

The curvature determination device can be, for example, a videokeratograph or a keratometer. The phase error measurement device can, for example, be designed as an autorefractor or wavefront sensor. The eye length calculating device and the ocular pivot point determination device can, for example, be implemented together in the form of a commercially available personal computer.

Another, second one of the apparatus mentioned initially herein is characterized by:
- a) a recording device for detecting the position and/or the shape of a characteristic part of the eye for at least two viewing directions, in the above-described sense;
- b) a determination device for determining the position of at least one characteristic axis of the eye for the two viewing directions from the position and/or the shape of the characteristic part of the eye;
- c) a determination device for determining the location of the ocular pivot point from the position of the characteristic axis of the eye for the two viewing directions.

The recording device can, for example, be a centering unit or a digital camera. The determination device and the ocular pivot point determination device can be implemented, for example, together in the form of a commercially available personal computer.

A further, third one of the apparatus mentioned at the beginning comprises:
- a) a measurement device for measuring in three dimensions at least a portion of the surface of the cornea of the eye for a first viewing direction of the test person, and for measuring in three dimensions at least a portion of the surface of the cornea for a second viewing direction of the test person altered by comparison with the first viewing direction at the same measurement position and for an unchanged head position of the test person; and,
- b) a computing device for describing the surface of the cornea determined in relation to the first viewing direction by a three-dimensional mathematical formula, and for determining the second viewing direction as well as the location of the ocular pivot point by fitting the measured three-dimensional data relating to the second viewing direction to the formula determined in relation to the first viewing direction, use being made of a mathematical transformation, in particular rotation about a point in space.

By way of example, a videokeratograph can be used as measurement device. The computing device can be, for example, a commercially available personal computer.

Finally, an inventive, fourth apparatus for determining at least two optical parameters of an eye having a reference structure is provided with separate recording units for photographically recording the eye for the determination of in each case one of the optical parameters of the eye. The recording units are designed in such a way that the reference structure of the eye is recorded in each case at the same time during the photographic recordings. At least one computing device is provided in order to refer the values of the parameters to the reference structure.

The object on which the invention is based is completely achieved in this way.

The first three methods are distinguished in that the location of the ocular pivot point can be determined even more exactly than conventionally. Consequently, a yet better optimization of, in particular, customized progressive lenses is possible when account is taken of the location of the ocular pivot point when calculating and producing the surface topography of the customized progressive lenses.

The mean curvature of the cornea, and the mean phase error of the eye can be determined without limitation at the penetration points of a given axis with the three-dimensional measurements of the corneal topography and/or wavefront errors of the eye.

The first to the third methods render it possible to achieve the above-named even better optimization by means of only a slight modification of known systems.

The fourth method renders possible a better referencing of two parameters recorded with different units, and thus incorrect adjustment of a pair of spectacles is avoided.

In the case of the first named inventive method, the location of the ocular pivot point ADL can be determined from the eye length LA by using the relationship:

$$ADL = k_3 LA \tag{1}$$

The quantity ADL specified in meters in this case specifies the distance between the corneal vertex lying on the fixation line and the center of the optical ocular pivot point Z'. The parameter $k_3$ is a prescribable, dimensionless parameter.

This parameter $k_3$ can, for example, be selected as 13.5/23.8 following the theory of Gullstrand. Deviations from this value of, for example, ±10% or 5%, can, however, be allowed in general.

In the case of this first named method, the eye length LA can, for example, be determined from the mean curvature KH and the mean phase error PF by using the relationship:

$$LA = (k_1 - PF) KH / k_2 \tag{2}$$

The mean curvature KH is generally specified in millimeters, and the mean phase error is generally specified in the dimension of diopters. The parameters $k_1$ and $k_2$ are freely prescribable in principle. The parameter $k_1$ has the dimension of the phase error, specifically in diopters, $k_2$ likewise has the dimension of diopters.

Following a theory of the inventors, $k_1$ is selected as 52.634 dpt and $k_2$ as 17.395 dpt. However, deviations from these values by ±10% or ±5% can generally be permitted. This measure has the advantage that an optimum determination of the location of the ocular pivot point is ensured for the by far predominant proportion of the population.

In this first-named method, it is generally sufficient in step a) to determine the mean curvature KH of the cornea in the region of the pupil opening. Since the expansion of the pupil opening depends on the ambient brightness, it is customary to take the region in diameter of 8 mm about the pupil center.

Since what is particularly important in the case of the curvature KH of the cornea and of the phase error PF is the region around the optical axis, it is generally the mean curvature KH of the cornea that is determined in step a), and the phase error PF in each case in the region around the optical axis and/or in the region around the fixation line and/or in the region around the visual axis of the eye, that is determined in step b). Typical radii about these axes are 4 mm. Radii of down to 2 mm or even 1 mm are also generally satisfactory. The normal to the front corneal surface, proposed for example in DIN 5340-, can be taken as the optical axis of the eye. The extension of the normal into the interior of the eye has the smallest distance from the center of curvature of the remaining refracting surfaces of the eye. The connecting straight line between the centrally imaged object point and its image point on the retina as proposed in DIN 5340-360 can be used as the visual axis (line of sight). By way of example, the connecting straight line proposed in DIN 5340-159 between the object point imaged in the fovea center and the middle of the entrance pupil of the eye can be used as fixation line.

These above-specified measures afford the advantage that the determination of the values is improved by virtue of the fact that these values are determined in a fashion spatially referred to one another, that is to say, referred to a specific axis or to the pupil center.

The phase errors can, for example, be measured by means of a wavefront refractor by using the Hartmann-Shack method. A mean value is then formed from the phase error distribution measured with the aid of the wavefront autorefractor. This mean value constitutes the mean phase error PF. The determination of the phase error with the aid of a wavefront autorefractor has the advantage that positional variations in the phase error are taken into account. An autorefractometer can also be used instead of a wavefront autorefractor.

In the case of the second method, the characteristic part of the eye can, for example, comprise the pupil and/or the limbus and/or the iris. These characteristic parts of the eye can be recognized by the naked eye, and can therefore be unambiguously identified in a simple way both by a user and by an automatic detection system. A misinterpretation is therefore largely excluded.

Instead of the above specified characteristic eye parts of pupil, limbus and/or iris, it is, of course, also possible to use other parts that are characteristic (in particular biometric ones) of the eye such as, for example, blood vessels or regions that can be distinguished by color. Such structures can even be referred in an individual case, for example, when what matters is the lack of invariance in the structure with reference to rotations.

The position and/or shape of the characteristic part of the eye can, for example, be detected by a calibrated photographic system. A calibrated photographic system is understood as a photographic system that can be used to detect three-dimensional parameters of the head/eye system. The use of such a system has the advantage that it can be used to measure with sufficient accuracy.

A calibrated video centering system, for example, can be used as calibrated photographic system. In general, a video centering system without calibration is merely a digital camera, and is therefore of no value for measuring operating parameters.

By way of example, the at least one characteristic axis whose position can be determined for the two viewing directions from the respective positions and/or the respective shapes of the characteristic part of the eye for the two viewing directions can comprise the fixation line and/or the visual axis and/or the optical axis. All three characteristics can, for example, be determined from the previously recorded data by simple computing operations by using the above-named method.

In the case of this second method, the determination of the location of the ocular pivot point can comprise a determination of the intersection point of the characteristic axes of the eye.

This second method can, for example, comprise the following steps:
 a) detecting the characteristic part of the eye and determining the geometric center thereof as well as the normal in the plane of the characteristic part at the center for a first viewing direction of the test person;
 b) detecting the characteristic part of the eye and determining the geometric center thereof as well as the normal in the plane of the characteristic part at the center for a second viewing direction, deviating from the first viewing direction, of the test person; and,
 c) determining the location of the ocular pivot point from the direction vectors of the normals determined in steps a) and b).

Instead of the intersection point of a characteristic axis in the case of different viewing directions, it is also possible to determine the two characteristic axes, and to determine the location of the ocular pivot point as an intersection point of the two characteristic axes.

Instead of the intersection point of two characteristic axes, it is also possible to determine more than two characteristic axes, and to determine the location of the ocular pivot point as the center of a spherical volume tangentially enclosed by the characteristic axes.

In order to determine the location of the ocular pivot point in the eye of a test person, one of the above described methods can be used as a method for optimizing a spectacle lens customized for an eye of a test person in which the location of the ocular pivot point is determined and used as input parameter.

The fourth inventive method can, for example, comprise the following steps:
 a) measuring a reference structure of the eye in a first measurement situation;
 b) measuring the reference structure of the eye in a second measurement situation;
 c) determining the change in position of the reference structure between the two measurement situations; and,
 d) correcting prescribed spectacle lenses as a function of the change in position.

This method is distinguished in that the measurements in accordance with a) and b) can reference one another. The method steps a) and b) can, for example, be carried out by the two recording devices. The method steps c) and d) can, for example, be executed by the computing device (for example a personal computer).

By way of example, in developments of this method the position of the pupil center of the eye and/or the position of the corneal vertex are/is determined in order to measure the reference structure. The position of the pupil center or the position of the corneal vertex are particularly suitable as reference structures, because they are easy to detect.

Also suitable as reference structures are, for example, a structure of the iris or blood vessels of the dermis. Such reference structures generally lack any kind of symmetry. It therefore permits an unambiguous localization in space.

A computer program with program code can be set up to carry out one of the above-described methods when the program is executed in a computer. The computer program can, for example, be stored on a machine-readable data medium.

The above-named features and the following ones still to be explained can be used not only in the combinations described but also in other combinations or on their own without departing from the scope of the present invention.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
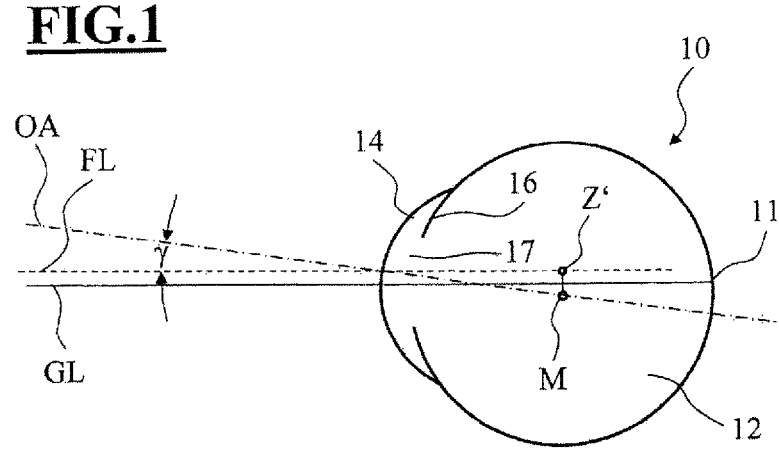
FIG. 1 shows a first schematic side elevation view of an upwardly rotated eye for the purpose of illustrating various viewing directions and pivot points and the location of the ocular pivot point.
Figure 2:
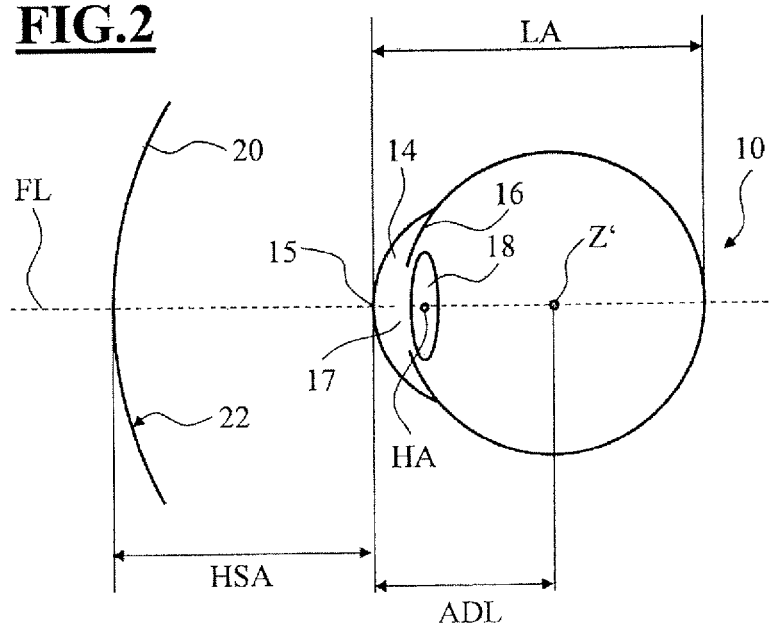
FIG. 2 shows a second schematic side view of an eye directed straight ahead, with a spectacle lens placed in front, for the purpose of explaining further parameters of the eye.

Reference numeral 10 denotes an eye in FIGS. 1 and 2. The eye 10 has a vitreous humor 12, a cornea 14, an iris 16, a pupil 17 and a lens 18.

When the eye 10 executes a rotary movement, this does not happen exactly about one pivot point in space; rather, there is merely an approximately spherical region in which the instantaneous pivot points are located. That point which experiences the slightest variation in position during eye movements is denoted as mechanical ocular pivot point M (compare DIN 5340-42).

GL denotes the viewing axis (line of sight). In accordance with DIN 5340-360, it is the connecting straight line between a fixed object point and the image point, conjugated therewith, in the middle of the fovea 11.

FL denotes the fixation line (line of sight). In accordance with DIN 5340-159, it is the connecting straight line between the centrally imaged object point and the center of the entrance pupil 17.

OA denotes the optical axis.

The optical ocular pivot point is denoted by Z'. According to DIN 5340-43, it is the foot of the perpendicular from the mechanical ocular pivot point M onto the fixation line FL.

The angle between the optical axis OA and the fixation line FL is denoted by γ in FIG. 1. Here, the angle γ is illustrated only in one plane and the solid angle is symbolized upward/downward and to the right/left.

A spectacle lens 20 is arranged in front of the eye 10 in FIG. 2. The spectacle lens has a rear surface 22 on the side facing the eye 10. The distance of the rear surface 22 from the corneal apex 15, measured in the viewing direction perpendicular to the frame plane is denoted as the corneal vertex distance HSA (compare DIN EN ISO 13666-5.27). The distance of the corneal apex 15 from the optical ocular pivot point Z' specifies the location of the ocular pivot point ADL with reference to the corneal apex 15.

The location of the ocular pivot point ADL is an important parameter in the calculation of the spectacle lens 20. The spectacle lens 20 is always optimized such that it has the optimum imaging properties for each viewing direction of the eye 10.

Figure 3:
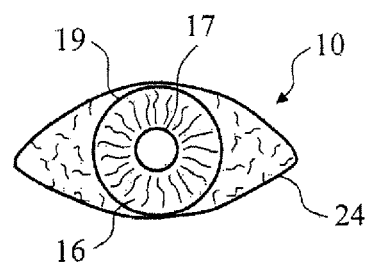
FIG. 3 shows a front view of an eye for the purpose of explaining specific eye regions.

FIG. 3 shows a front view of the eye 10. A characteristic structure is to be recognized in the iris 17, and a structure of small blood vessels in the dermis 24 is to be recognized in addition to the iris 17.

First Embodiment

Figure 11:
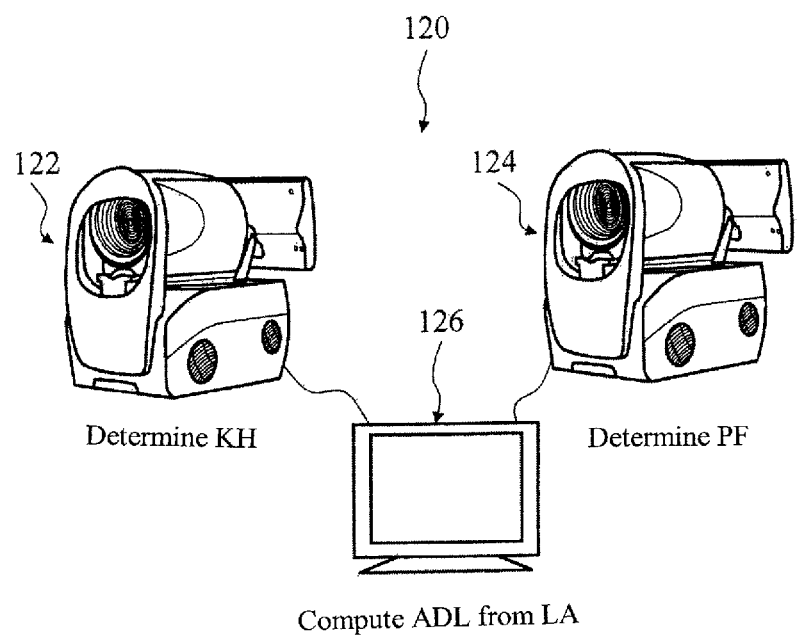
FIG. 11 shows an apparatus for determining the location of the ocular pivot point in an eye of a test person, in accordance with the invention.

In the case of a first embodiment of an inventive method, the location of the ocular pivot point ADL is determined on the basis of an eye model and an estimate of the eye length LA. An inventive device 120 for carrying out the method is shown in FIG. 11. The method comprises the steps set forth below.

In a first step 1a), a unit 122, specifically a suitable scanner, is used to determine the topography of the cornea 14, and from that the mean curvature KH of the cornea 14. It is possible during this measurement for the location of the center of the pupil 17 to be determined at the same time in addition to the position of the vertex of the cornea 14.

Figure 4:
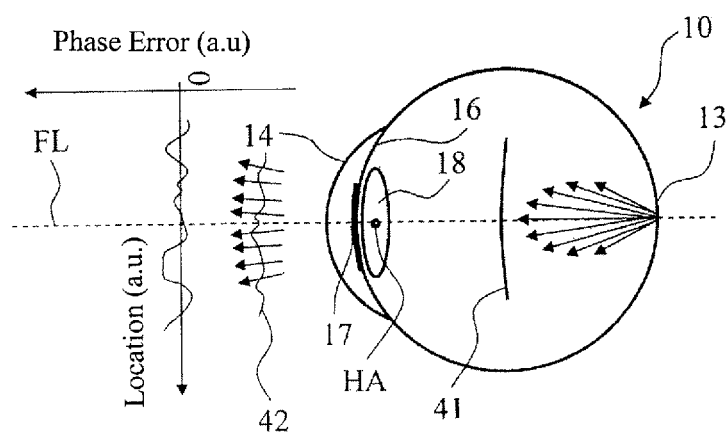
FIG. 4 shows a third schematic side elevation view of an eye directed straight ahead for the purpose of explaining the measurement of the phase error of the eye with the aid of a wavefront autorefractor and wherein the axes are in arbitrary units (a.u.)

In a second step 1b), the phase errors and the mean value of the phase error PF of the eye 10 are determined. Use is made for this purpose of, for example, a wavefront autorefractor 124 of known design, which determines the distribution of the phase errors over the entire opening of the pupil 17 of the eye 10, as is illustrated in FIG. 4. The phase error distribution can, for example, be determined with the aid of the so-called standard Hartmann-Shack method. This method is based on the comparison of a wavefront 42, which has been scattered on the retina 13 and entered through the eye, with the wavefront 41 before the scattering and the passage through the eye. The position of the center of the pupil 17 can also be determined in this case. The two measurements can, if appropriate, also be carried out with the aid of two different measurement arrangements in a unit (for this reason, FIG. 11 shows two identical units (122, 124)). A computer 126 then computes the arithmetic mean value of the phase error PF of the eye 10 of the test person from the distribution of the phase errors over the location.

In order to produce a common reference system for the measured positions in the two above-named steps, it is possible according to the invention to produce additionally in each of the two steps 1a) and 1b) a photographic recording that detects, for example, the structures, illustrated in FIG. 3, of the iris 16 or of the blood vessels in the dermis 24. These structures can then be used as a reference system for the positions of the pupil center and of the corneal vertex as well as further parameters.

In step 1c), the eye length LA is now determined from the values KH and PF thus determined. Use may be made for this purpose of the relationship:

$$LA = (k_1 - KR) KH/k_2,$$

wherein constants $k_1$ and $k_2$ are obtained from a model that is/has been set up from measurements on a multiplicity of eyes.

Figure 5:
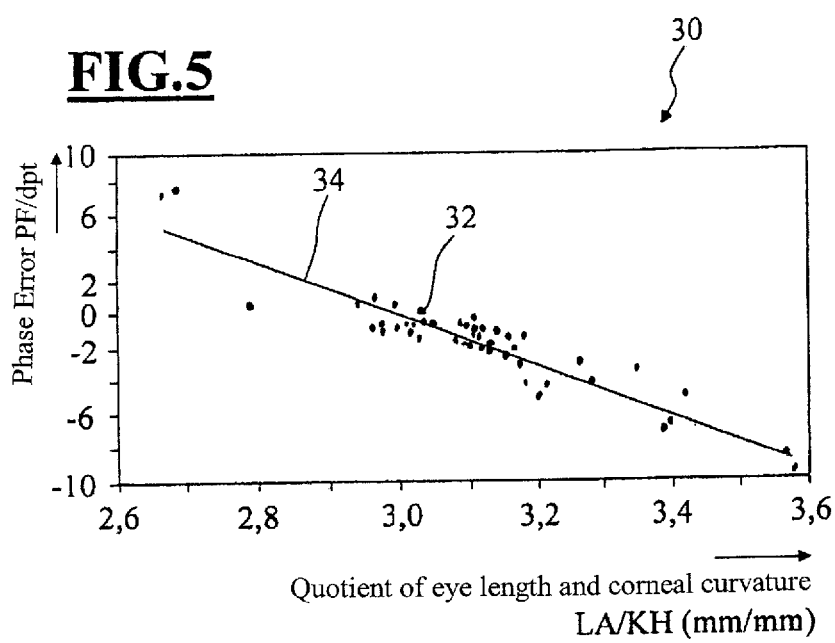
FIG. 5 shows how a diagram can be used in the context of the first method of the present invention to determine the location of the ocular pivot point and wherein the axes are in arbitrary units (a.u.)

To this end, FIG. 5 shows a diagram 30 with the relationship between the quotient of eye length and corneal curvature (abscissa LA/KH) and the phase error of the eye (ordinate PF). The points denote the results of real measurements on test persons. The mean straight line 34 reproduces the linear relationship between the measured values.

The constants $k_1$ and $k_2$ can be gathered from the profile of the straight line 34 as follows:

$$k_1 = 52.634 \; dpt$$

$$k_2 = 17.395 \; dpt.$$

In a fourth step 1d), the eye length LA thus determined can be used to determine the location of the ocular pivot point ADL in accordance with the relationship $$ADL = k_3 LA,$$

it being the case, for example, that according to Gullstrand the empirical value is:

$$k_3 = 13.5/23.8.$$

The location of the ocular pivot point ADL determined in such a way can be used as input parameter in the calculation of a spectacle lens optimized in a customized fashion.

It is preferred in step a) to determine the mean curvature KH of the cornea 14 in the region of the pupil opening. Alternatively, or in addition, it is possible to determine the mean curvature KH of the cornea 14 in step a), and the phase error PF in the particular region around an axis (OA, GL) of the eye 10 in step b). The mean curvature KH of the cornea 14 is determined particularly in this case in a region of diameter 12 mm about the corneal vertex, while the mean phase error PF is determined in a corresponding region around the pupil center. The two values are spatially referenced in this way, that is to say, the two are referred to a specific characteristic axis OA or GL or to the pupil center, for example.

Second Embodiment

In accordance with a second embodiment of an inventive method, it is also possible to detect the position and/or the shape of a characteristic part of the eye in at least two viewing directions, and to determine therefrom, in turn, the position of at least one characteristic axis of the eye for these two viewing directions, and to determine the location of the ocular pivot point with the aid of this/these characteristic axis/axes of the eye for the two viewing directions.

The location of the ocular pivot point determined in such a way can then be used, in turn, as input parameter in the calculation of a spectacle lens optimized in customized fashion.

The first variant, specifically the determination of the location of the ocular pivot point from the position of a characteristic part of the eye takes place as set forth below.

Figure 12:
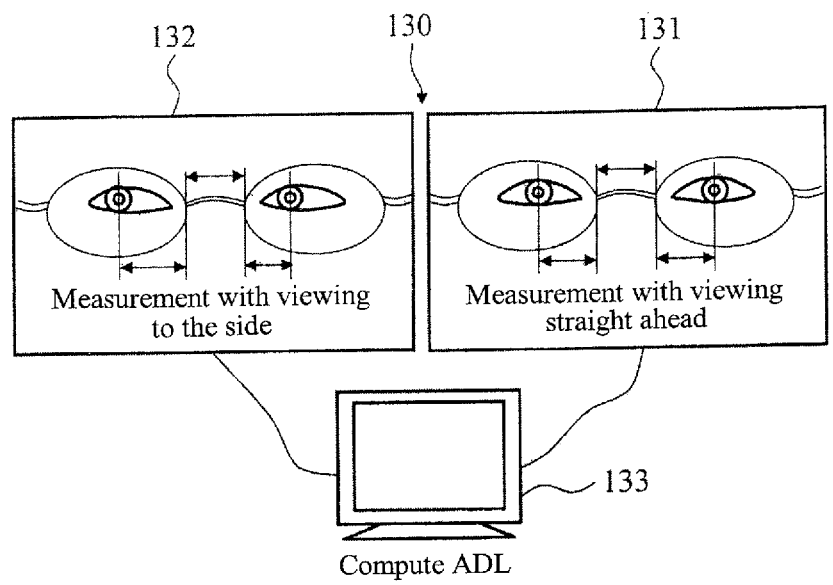
FIG. 12 shows another apparatus for determining the location of the ocular pivot point in accordance with the invention.

The test person is charged with looking at a specific fixation target. A calibrated photographic system is used to record the eye for this viewing direction. Such a calibrated photographic system can be a video centering system such as is marketed by Carl Zeiss Vision GmbH of Aalen, Germany, under the designations "RVT" and "i.Terminal". To this end, the video centering system need only be set such that it can record images of the eye 10 in different viewing directions. The reference numerals 131 in FIG. 12 characterize a recording of such a video centering system for the straight ahead viewing direction.

The test person is then charged with looking at a fixation target in another viewing direction. The calibrated photographic system is used to record the eye anew for this second viewing direction. The reference numeral 132 in FIG. 12 characterizes a recording of the video centering system for the lateral viewing direction. These recordings are then used to determine the position of the characteristic eye part such as, for example, the pupil (particularly the pupil center), the iris, the limbus, a blood vessel or the like, for example, by means of a computer 133. Characteristic eye axes such as, for example, the fixation line FL and/or the viewing axis GL and/or the optical axis OA can be determined in each case for the different viewing directions γ from the knowledge concerning the different viewing directions γ, that is to say, the extent to which the particular fixation point, and the particular position of the characteristic eye part obtained from the recordings, is known. These then serve for determining the location of the ocular pivot point ADL.

By way of example, in a first step 2a) the position of the pupil 17 and of the pupil center is specifically recorded, with the test person looking, for example, straight ahead. The normal to the pupil plane at the pupil center is determined therefrom, and thus a first viewing direction $\gamma_1$ is determined.

In a second step 2b), the position of the pupil 17 and of the pupil center is recorded, with the test person now looking to the side. The normal to the pupil plane at the pupil center is again determined therefrom, and thus a second viewing direction $\gamma_2$ is determined.

In a third step 2c), the ocular pivot point Z', that is to say, the location of the ocular pivot point ADL, is now determined as intersection point of the two normal vectors from the two different viewing directions ($\gamma_1$, $\gamma_2$).

Given recordings from more than two viewing directions γ, it is also possible to determine the extended, in general approximately spherical zone already mentioned, in which the instantaneous ocular pivot points are located.

The second variant, specifically the determination of the location of the ocular pivot point from the shape of a characteristic part of the eye is described below:

As in the case of the preceding variant, a calibrated photographic system is used to record the eye for different viewing directions γ. These recordings are then used to determine the shape of the characteristic eye part such as, for example, the pupil, the iris, the blood vessels or the like. Characteristic axes can be derived from these shapes. Otherwise than in the case of the previously described variant, there is no need with this method variant to know the different fixation targets for the different viewing directions γ. The axes then serve, in turn, for determining the location of the ocular pivot point.

The location of the ocular pivot point is accordingly determined from a mathematical transformation on the eye 10 given a different viewing direction γ, and a calibrated photographic system is used for the mathematical transformation.

Third Embodiment

Figure 13:
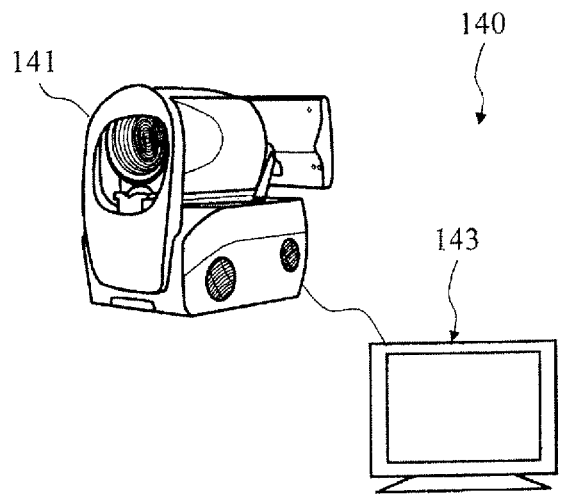
FIG. 13 shows a further apparatus for determining the location of the ocular pivot point in accordance with the invention; and, FIG. 14 shows an apparatus for determining at least two optical parameters of an eye, in accordance with the invention.

In the case of a third embodiment of an inventive method, the surface of the cornea 14 is measured in three dimensions in a first step 3a), for example, given that the test person is looking in a direction straight ahead. This can be done, for example, by means of a unit such as marketed by Carl Zeiss Vision GmbH under the designation of "iProfiler". FIG. 13 outlines an arrangement 140 for carrying out the method. The "iProfiler" is denoted by the reference numeral 141 in FIG. 13.

Figure 6:
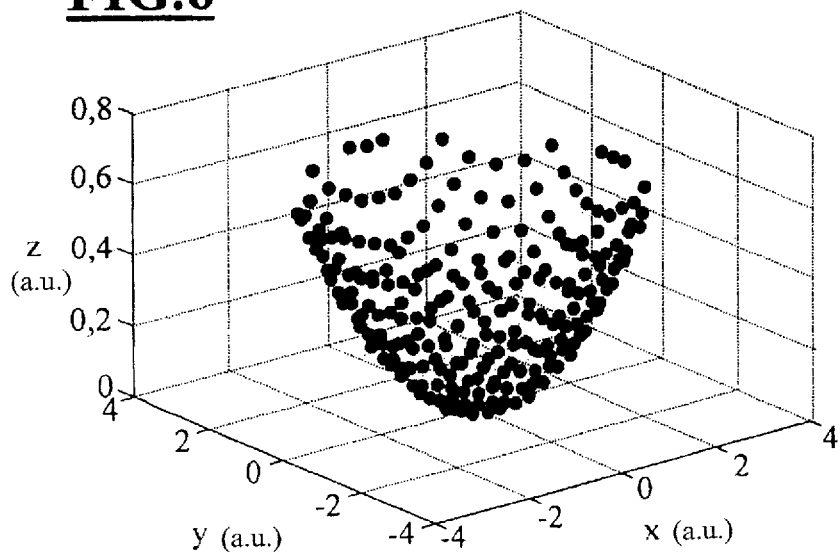
FIG. 6 shows an illustration of a pointwise measurement of the cornea in the case when the test person looks straight ahead and wherein the axes are in arbitrary units (a.u.)

FIG. 6 shows an exemplary illustration of the points that are measured on the cornea 14 in the case of a look directed straight ahead. The Z-axis, directed upwardly, coincides with this viewing direction.

In a second step 3b), the surface of the cornea 14 determined in the first step is described, for example, in a computer 143 by a three-dimensional mathematical formula.

The customary mathematical methods can be used to determine this formula. An example of this is the approximation of the fitting to the points by a least squares fit, for example. This approximation is described, for example, in the instructions relating to the "lsqnonlin" function of the MATLAB software packet from The MathWorks, Inc. A further example is suitable mathematical function classes such as Zernike polynomials and splines.

Figure 7:
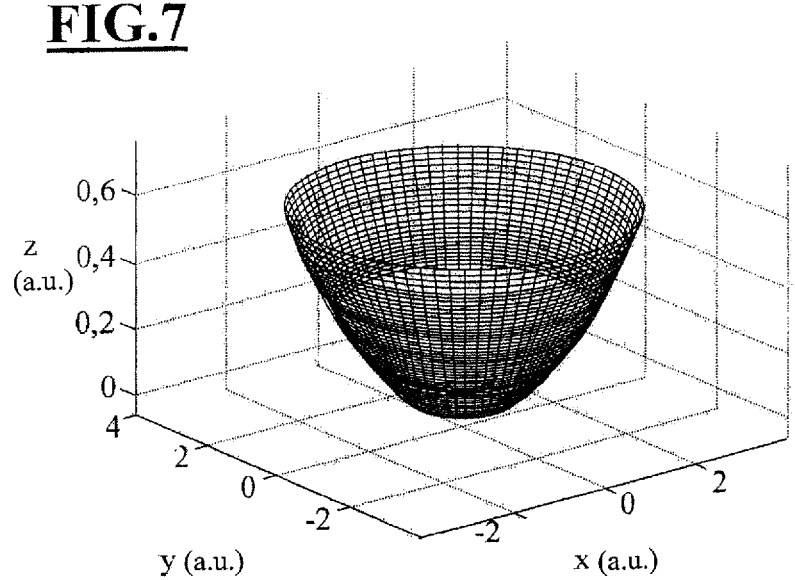
FIG. 7 shows an illustration of the three-dimensional mathematical function for describing the cornea of FIG. 6 and wherein the axes are in arbitrary units (a.u.)

FIG. 7 shows the surface resulting from the approximation made in step 3b) to the corneal data. It is now possible to use the fundamental mathematical description to calculate a point on the cornea 14 for each arbitrary point of the region of the cornea 14 measured in step 3b).

In a third step 3c), at least a portion of the surface of the cornea 14 is measured in three dimensions in the same measurement position as in step 3a) given a test person looking with an inclination by an angle γ.

Figure 8:
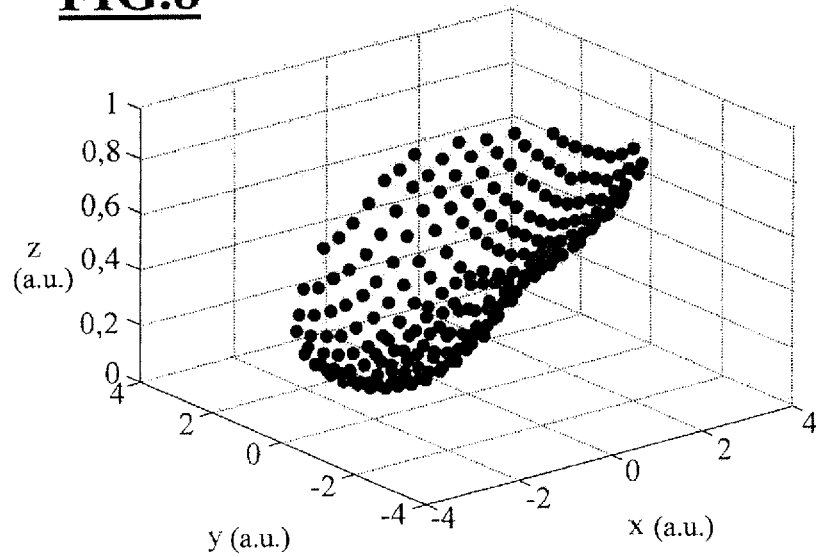
FIG. 8 shows an illustration of a pointwise measurement of the cornea in the case when the test person looks in a direction other than in FIG. 6 and wherein the axes are in arbitrary units (a.u.)

FIG. 8 explains step 3c). In the illustrated embodiment, the same measurement range as in step 3a) is used for measuring the eye 10 for an altered viewing direction γ. This means that a portion of the corneal surface measured in step 3a) departs from the measurement range and portions of the dermis 24 come into the measurement range. This is explained in FIG. 8 by the easily recognizable kink in the profile of the measurement points.

Figure 9:
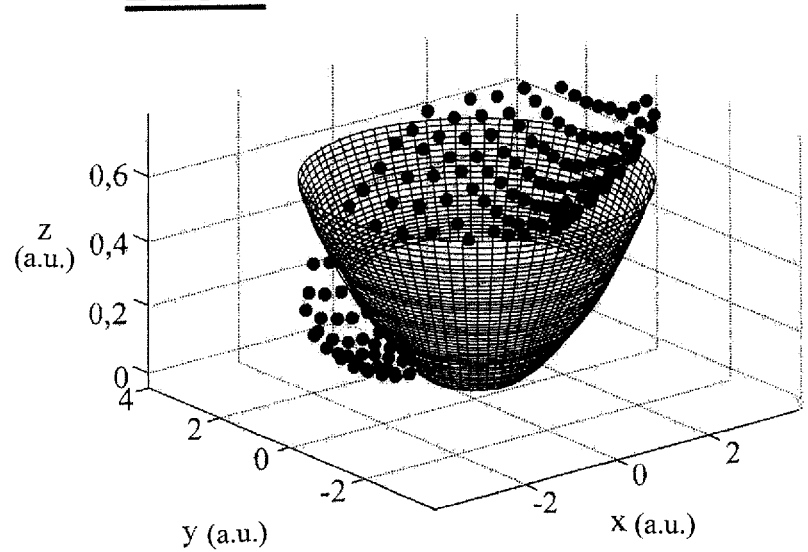
FIG. 9 shows an illustration of the corneal points for the viewing direction in accordance with FIG. 8 by comparison with the viewing direction in accordance with FIG. 6 and wherein the axes are in arbitrary units (a.u.)

FIG. 9 shows the position of the corneal points measured in step 3c) for an altered viewing direction γ by comparison with the position of the corneal points in step 3a).

In a fourth step 3d), the angles of the viewing directions γ and the location of the ocular pivot point ADL are determined by fitting the three-dimensional data determined in step 3c) to the formula determined in step 3b).

This is done by applying a rotation about a point in space to which the data determined in step 3c) are subjected until they are brought to coincide as well as possible with the mathematical description of the corneal surface determined in step 3b). The viewing direction γ (vector) and the position of the location of the ocular pivot point ADL are used in this method as free parameters of the approximation (for example, least squares fit) to the mathematical description of the corneal surface previously determined in step 3b). The location of the ocular pivot point ADL and the viewing direction γ have been found once the best fit is achieved. Consequently, there is no need in this method to prescribe a specific viewing direction γ to the test person. It also suffices to measure only a portion of the corneal surface in step 3c). All that is important is also to measure in step 3c) a region of the cornea 14 that has already been measured in step 3a) and been included in the determination of the mathematical formula in step 3b).

Figure 10:
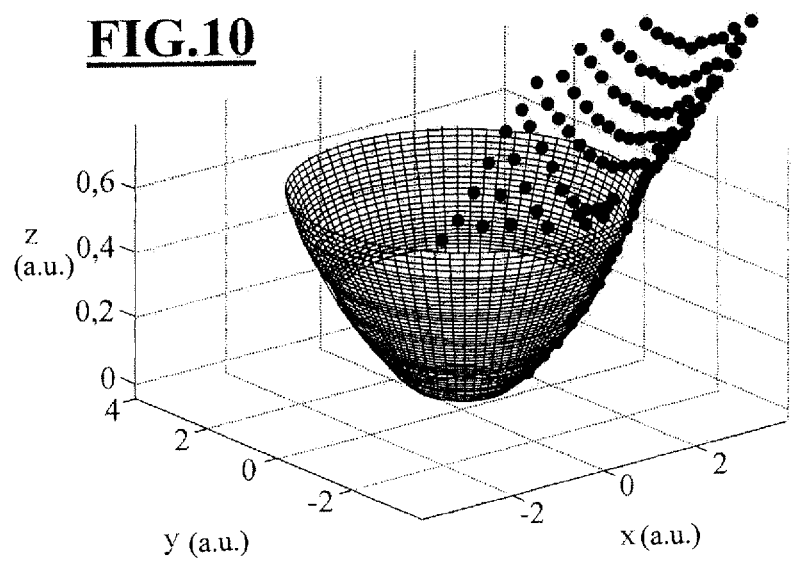
FIG. 10 shows an illustration of the results after a fitting of the corneal points in accordance with FIG. 9 to the mathematical function in accordance with FIG. 7 and wherein the axes are in arbitrary units (a.u.)

FIG. 10 shows the result of the approximation carried out in step 3d). The measurement points determined in step 3c) have been brought up as well as possible to the surface found in step 3b) by rotation about a point in space (ocular pivot point). The portion of the dermis 24 also measured in the example related to step 3c), that is to say, FIG. 8, lies at the correct point outside the cornea 14.

Fourth Embodiment

Figure 14:
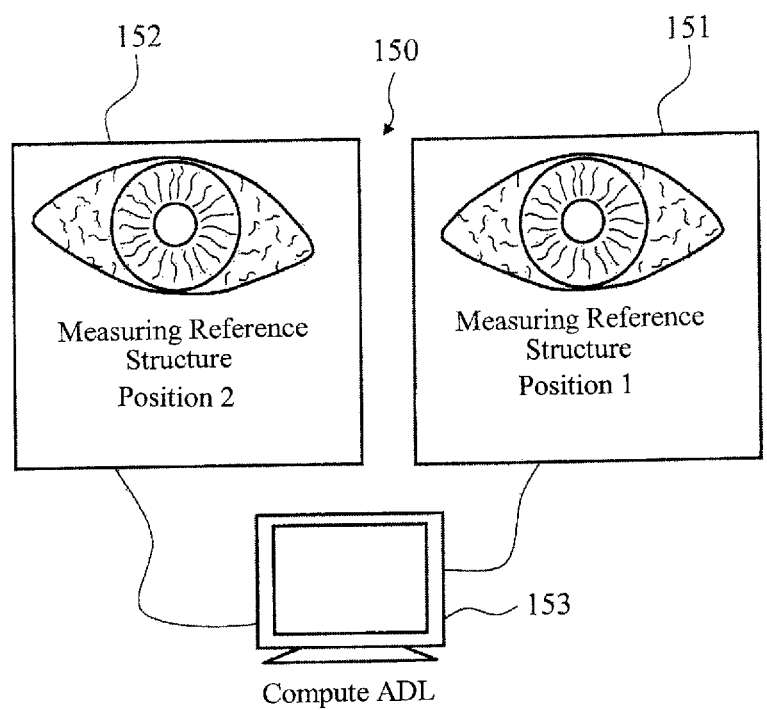

In a fourth embodiment of an inventive method, a reference structure of the eye 10 is detected in general in a first step 4a) in a first measurement situation. The corresponding arrangement 150 is illustrated in FIG. 14. In this case, the reference structure is a structure of the iris 16 or a structure of blood vessels in the dermis 24 (compare reference numeral 151).

In a second step 4b), the reference structure of the eye 10 is detected in a second measurement situation. The first and the second measurement situations are to be understood to mean that two different measurements have been undertaken and/or that two different measurement methods have been used, preferably by means of different measurement units (151, 152).

In a third step 4c), the change in position, in particular the rotation between the measurement situations in steps 4a) and 4b), is determined computationally (computer 153) and taken into account when prescribing the spectacle lens 20.

According to the invention, a photographic recording of the reference structures can be produced in each of the steps 4a) and 4b) in order to produce a common reference system for the measured positions of the reference structures in steps 4a) to 4c). The reference structures can then be used as a common reference system for the positions of the pupil center and of the corneal vertex as well as further parameters.

This method is suitable, for example, for referencing the two recordings of the eye given different viewing directions such as are necessary for the second and third methods.

It is understood that the foregoing description is that of the preferred embodiments of the invention and that various changes and modifications may be made thereto without departing from the spirit and scope of the invention as defined in the appended claims.

LIST OF REFERENCE CHARACTERS

10 Eye
11 Fovea
12 Vitreous humor
13 Retinal plane
14 Cornea
15 Corneal vertex
16 Iris
17 Pupil
18 Lens
19 Limbus
20 Spectacle lens
22 Rear surface
24 Dermis
30 Diagram
32 Measurement point
34 Straight line
41 Wavefront
42 Wavefront
120 Apparatus for determining the location of the ocular pivot point
122 iProfiler
124 iProfiler
126 Computer
130 Apparatus for determining the location of the ocular pivot point
131 Video centering unit (recorder 1)
132 Video centering unit (recorder 2)
133 Computer
140 Apparatus for determining the location of the ocular pivot point
141 iProfiler
143 Computer
150 Apparatus for determining at least 2 optical parameters
151 Video centering unit (recorder 1)
152 Video centering unit (recorder 2)
153 Computer
ADL Location of the ocular pivot point
HA Object-side main point of the eye
HSA Corneal vertex distance
FL Fixation line
GL Visual axis
PF Mean phase error
KH Curvature of the cornea
LA Eye length
M Mechanical ocular pivot point
OA Optical axis
Z' Optical ocular pivot point
x,y,z Spatial coordinates
γ Angle, viewing direction

What is claimed is:

1. A method for providing a spectacle lens by determining at least two mutually different optical parameters of an eye defining a reference structure of the eye itself, the method comprising:

providing a first measuring device for determining a first one of said at least two mutually different optical parameters of the eye in a first measurement situation in a first viewing direction of the eye while simultaneously recording said reference structure of said eye;

providing a second measuring device configured differently from said first measuring device for determining a second one of said at least two mutually different optical parameters in a second measurement situation in a second viewing direction of the eye while simultaneously recording said reference structure;

measuring said reference structure of the eye in the first measurement situation by making a photographic recording of the eye with said first measuring device while determining the first optical parameter;

measuring said reference structure of the eye in the second measurement situation by making a photographic recording of the eye with said second measuring device while determining the second optical parameter;

referring the values of said optical parameters to said reference structure obtained in corresponding ones of said first and second measuring situations;

determining a change in position of said reference structure as photographically recorded in said first measurement situation and in said second measurement situation; and, correcting prescribed spectacle lenses in dependence upon the determined change in position of said reference structure as photographically recorded in said first measurement situation and in said second measurement situation.

2. The method of claim 1, wherein said reference structure is the pupil center of the eye; and, the position of the pupil center of the eye is measured.

3. The method of claim 1, wherein said reference structure is the corneal vertex of the eye; and, the position of the corneal vertex is determined.

4. The method of claim 1, wherein the reference structure is a structure of the iris or of blood vessels of the dermis.

5. The method of claim 1, wherein the reference structure is a structure of the iris and of blood vessels of the dermis.

6. A system for providing a spectacle lens by determining at least two mutually different optical parameters of an eye defining a reference structure of the eye itself, the system comprising:

a first measuring unit for determining a first one of said mutually different optical parameters of the eye in a first measurement situation in a first viewing direction of the eye while simultaneously recording said reference structure;

a second measuring unit configured differently from said first measuring unit for determining a second one of said at least two mutually different optical parameters in a second measurement situation in a second viewing direction of the eye while simultaneously recording said reference structure;

said first measuring unit being configured to photographically record said reference structure in said first measurement situation while determining the first optical parameter;

said second measuring unit being configured to photographically record said reference structure in said second measurement situation while determining the second optical parameter; and, a computing unit for referring the values of said parameters to said reference structure obtained in corresponding ones of said first and second measuring situations, and for determining a change in position of said reference structure as photographically recorded in said first measurement situation and in said second measurement situation and for correcting prescribed spectacle lenses in dependence upon the determined change in position of said reference structure as photographically recorded in said first measurement situation and in said second measurement situation.

7. A computer program stored on a non-transitory machine-readable data medium having a program code set up to carry out a method for prescribing a spectacle lens by determining at least two mutually different optical parameters of an eye defining a reference structure of the eye itself when the program is executed on a computer with the method comprising:

providing a first measuring device for determining a first one of said at least two mutually different optical parameters in a first measurement situation in a first viewing direction of the eye while simultaneously recording said reference structure;

providing a second measuring device configured differently from said first measuring device for determining a second one of said at least two optical parameters in a second measurement situation in a second viewing direction of the eye while simultaneously recording said reference structure;

measuring said reference structure of the eye in the first measurement situation by making a photographic recording of the eye with said first measuring device while determining the first optical parameter;

measuring said reference structure of the eye in the second measurement situation by making a photographic recording of the eye with said second measuring device while determining the second optical parameter;

referring the values of said parameters to said reference structure obtained in corresponding ones of said first and second measuring situations;

determining a change in position of said reference structure as being photographically recorded in said first measurement situation and in said second measurement situation; and, correcting prescribed spectacle lenses in dependence upon the determined change in position of said reference structure as photographically recorded in said first measurement situation and in said second measurement situation.

8. The computer program of claim 7, wherein said reference structure is the pupil center of the eye; and, the position of the pupil center of the eye is measured.

9. The computer program of claim 7, wherein said reference structure is the corneal vertex of the eye; and, the position of the corneal vertex is determined.

10. The computer program of claim 7, wherein the reference structure is a structure of the iris or of blood vessels of the dermis.

11. The computer program of claim 7, wherein the reference structure is a structure of the iris and of blood vessels of the dermis.

* * * * *

UNITED STATES PATENT AND TRADEMARK OFFICE
CERTIFICATE OF CORRECTION

PATENT NO. : 10,433,724 B2
APPLICATION NO. : 14/459154
DATED : October 8, 2019
INVENTOR(S) : T. Kratzer et al.

It is certified that error appears in the above-identified patent and that said Letters Patent is hereby corrected as shown below:

On the Title Page

Page 2:
Item (56) OTHER PUBLICATIONS, Grimm W. et al: delete "issues 4 and May 2000." and insert -- issues 4 and 5 / 2000. -- therefor.

In the Specification

In Column 1:
Line 50: delete "and" and insert -- und -- therefor.

Signed and Sealed this
Twenty-fourth Day of November, 2020

Andrei Iancu
*Director of the United States Patent and Trademark Office*